US012751623B2

(12) United States Patent
Kostakis et al.

(10) Patent No.: US 12,751,623 B2
(45) Date of Patent: Oct. 6, 2026

(54) THERMAL BIMETAL ACTUATORS FOR USE IN NON-MAGNETIC MEDICAL DEVICES

(71) Applicant: KONINKLIJKE PHILIPS N.V., Eindhoven (NL)

(72) Inventors: Dimitri George Kostakis, Orlando, FL (US); Bruce Geoffrey Appleton, Orlando, FL (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 276 days.

(21) Appl. No.: 18/720,764

(22) PCT Filed: Dec. 8, 2022

(86) PCT No.: PCT/EP2022/085016

§ 371 (c)(1),
(2) Date: Jun. 17, 2024

(87) PCT Pub. No.: WO2023/110631

PCT Pub. Date: Jun. 22, 2023

(65) Prior Publication Data

US 2025/0049321 A1 Feb. 13, 2025

Related U.S. Application Data

(60) Provisional application No. 63/290,866, filed on Dec. 17, 2021.

(51) Int. Cl.
*A61B 5/00* (2006.01)
*A61B 5/055* (2006.01)
(Continued)

(52) U.S. Cl.
CPC ............ *A61B 5/0036* (2018.08); *A61B 5/055* (2013.01); *F16K 31/002* (2013.01); *H02N 11/006* (2013.01)

(58) Field of Classification Search
CPC ..... A61B 5/0036; A61B 5/055; F16K 31/002; H02N 11/006
(Continued)

(56) References Cited

U.S. PATENT DOCUMENTS

| | | | |
|---|---|---|---|
| 5,318,268 | A | 6/1994 | Cox |
| 7,632,245 | B1 | 12/2009 | Cowan |

(Continued)

FOREIGN PATENT DOCUMENTS

| | | | |
|---|---|---|---|
| DE | 2460267 | A1 | 7/1975 |
| DE | 19926742 | A1 | 1/2000 |

(Continued)

OTHER PUBLICATIONS

International Search Report Dated Mar. 30, 2023 for International Appln No. PCT/EP2022/085016 Filed Dec. 8, 2022.

(Continued)

*Primary Examiner* — Walter L Lindsay, Jr.
*Assistant Examiner* — Frederick Wenderoth

(57) ABSTRACT

Non-magnetic thermally-controlled bimetal valves comprising active and passive members having different coefficients of thermal expansion, and systems incorporating such valves, are described herein. These valves and systems find particular application in the field of patient care as it relates to magnetic resonance ("MR") environments, such as environments with strong electromagnetic fields generated by MR imaging machines.

11 Claims, 5 Drawing Sheets

(51) Int. Cl.
*F16K 31/00* (2006.01)
*H02N 11/00* (2006.01)

(58) Field of Classification Search
USPC .......................................................... 324/322
See application file for complete search history.

(56) References Cited

U.S. PATENT DOCUMENTS

| | | | |
|---|---|---|---|
| 9,562,621 | B2 | 2/2017 | O'Neill et al. |
| 10,016,140 | B2 | 7/2018 | O'Neill |
| 2010/0331667 | A1 | 12/2010 | Nelson |
| 2016/0053909 | A1 | 2/2016 | O'Neill |
| 2017/0261239 | A1 | 9/2017 | Tigwell |

FOREIGN PATENT DOCUMENTS

| | | | | |
|---|---|---|---|---|
| WO | WO-2014178726 | A1 * | 11/2014 | .......... H10W 74/016 |
| WO | 2019166316 | A1 | 9/2019 | |

OTHER PUBLICATIONS (2008) Kanthal Thermostatic Bimetal Handbook.
Engineered Materials Solutoins, LLC Thermostatic Bimetal Designer's Guide].

* cited by examiner

THERMAL BIMETAL ACTUATORS FOR USE IN NON-MAGNETIC MEDICAL DEVICES

CROSS-REFERENCE TO PRIOR APPLICATIONS

This application is the U.S. National Phase application under 35 U.S.C. § 371 of International Application No. PCT/EP2022/085016, filed on Dec. 8, 2022, which claims the benefit of U.S. Provisional Application No. 63/290,866 filed Dec. 17, 2021. These applications are hereby incorporated by reference herein.

FIELD OF THE DISCLOSURE

The present disclosure is directed generally to thermal actuators and systems incorporating such actuators, and more specifically, non-magnetic thermal bimetal valves for use in environments subjected to strong magnetic fields.

BACKGROUND

In many technological fields, progress often drives the design of increasingly miniaturized components and subsystems. At the same time, within the field of medical devices, there is an equally important need for safety control and risk mitigation. This need is especially heightened in specialized medical settings where patients are exposed to strong electromagnetic fields, such as in magnetic resonance ("MR") environments.

Powerful magnetic fields make the MR environment very different from other care areas. In particular, the electromagnetic fields generated by powerful magnets within MR environments can significantly affect operation of nearby objects, including medical devices. General purpose medical devices (or components thereof) can not only diminish the quality of care provided but can also endanger the safety and health of patients and those nearby. Because additional care must be taken to design and manufacture medical devices and medical device components intended for use in MR environments, these devices and components can often be more expensive than general purpose accessories.

When designing for high magnetic field strengths, components and materials that work at these high fields are limited. One example of a device that must be specially designed, engineered, and manufactured to withstand the challenges of MR environments include includes fluid valves (e.g., for air, gas, liquids, etc.), which may be used in a variety of medical devices and patient monitoring systems. Standard valves use a coiled spring mechanism to actuate a plunger to open and close the valve. The coil is usually made of a magnetic material so the high magnetic field will either pull the valve open or closed and not allow it to do the opposite.

Current approaches to such valves include incorporating piezo technology and/or shape memory alloy (SMA) designs. However, other valve actuators that function within extreme magnetic fields, possess minimal overall size, and do not compromise the quality of care or patient safety are desired.

SUMMARY OF THE DISCLOSURE

The present disclosure is directed generally to inventive thermal actuators and valves, such as thermal bimetal actuators intended for use in magnetic resonance ("MR") environments. The present disclosure is further directed to systems incorporating such actuators and valves.

In accordance with one embodiment of the present disclosure, provided is a non-magnetic thermally-controllable valve comprising: a valve housing having an inlet, an outlet, and an open interior volume; and a bimetal actuator disposed within the open interior volume of the valve housing and forming a fluid-tight seal with at least one of the inlet and the outlet. The bimetal actuator may include an active member and a passive member, wherein the active member may be physically joined to the passive member.

In accordance with an aspect of the present disclosure, the active member may comprise a first non-magnetic metal and/or metal alloy and have a first coefficient of thermal expansion.

In accordance with an aspect of the present disclosure, the passive member may comprise a second non-magnetic metal and/or metal alloy and have a second coefficient of thermal expansion.

In accordance with an aspect of the present disclosure, the first coefficient of thermal expansion may be greater than the second coefficient of thermal expansion.

In accordance with an aspect of the present disclosure, the first non-magnetic metal and/or metal alloy may comprise at least one of magnesium, manganese, nickel, titanium, copper, and the like.

In accordance with an aspect of the present disclosure, the second non-magnetic metal and/or metal alloy may comprise at least one of magnesium, manganese, nickel, titanium, copper, and the like.

In accordance with an aspect of the present disclosure, the first non-magnetic metal and/or metal alloy may be substantially free from at least one of iron, nickel, cobalt, steel, and the like.

In accordance with an aspect of the present disclosure, the second non-magnetic metal and/or metal alloy may be substantially free from at least one of iron, nickel, cobalt, steel, and the like.

In accordance with an aspect of the present disclosure, the ratio of the first coefficient of thermal expansion to the second coefficient of thermal expansion may be from about 11:10 to about 100:1.

In accordance with an aspect of the present disclosure, the active member may be at least one of: a cantilever beam; a disc; and a plunger.

In accordance with an aspect of the present disclosure, the passive member may be at least one of: a cantilever beam; a disc; and a plunger.

In accordance with another embodiment of the present disclosure, provided is a magnetic resonance system comprising: a magnetic resonance device; a fluid flow device comprising a non-magnetic thermally-controlled valve having a bimetal actuator; and a valve controller operatively connected to the non-magnetic thermally-controlled valve, wherein the valve controller is configured to actuate the bimetal actuator of the non-magnetic thermally-controlled valve. The non-magnetic thermally-controlled valve may include: a valve housing comprising an inlet, an outlet, and an open interior volume; and a bimetal actuator disposed within the open interior volume of the valve housing and forming a fluid-tight seal with at least one of the inlet and the outlet, wherein the bimetal actuator includes an active member and a passive member. According to the present disclosure, the active member may be physically joined to the passive member.

In accordance with an aspect of the present disclosure, the active member may comprise a first non-magnetic metal and/or metal alloy and have a first coefficient of thermal expansion, the passive member may comprise a second non-magnetic metal and/or metal alloy and have a second coefficient of thermal expansion, and the first coefficient of thermal expansion may be greater than the second coefficient of thermal expansion.

In accordance with an aspect of the present disclosure, the ratio of the first coefficient of thermal expansion to the second coefficient of thermal expansion may be from about 11:10 to about 100:1.

In accordance with an aspect of the present disclosure, the first non-magnetic metal and/or metal alloy comprises at least one of magnesium, manganese, nickel, titanium, copper, and the like.

In accordance with an aspect of the present disclosure, the second non-magnetic metal and/or metal alloy comprises at least one of magnesium, manganese, nickel, titanium, copper, and the like.

In accordance with an aspect of the present disclosure, the first non-magnetic metal and/or metal alloy is substantially free from at least one of iron, nickel, cobalt, steel, and the like.

In accordance with an aspect of the present disclosure, the second non-magnetic metal and/or metal alloy is substantially free from at least one of, iron, nickel, cobalt, steel, and the like.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments of non-magnetic thermally-controlled bimetal valves and systems incorporating such valves, including patient monitoring systems for use in magnetic resonance ("MR") environments. As used herein, the term "non-magnetic" refers to the ability of a material, such as a metal or metal alloy, to be non-ferromagnetic and exhibit little to no movement or heating due to the presence of a strong magnetic field when used in the thermally-controlled bimetal valves and valve systems according to the present disclosure.

Figure 1A:
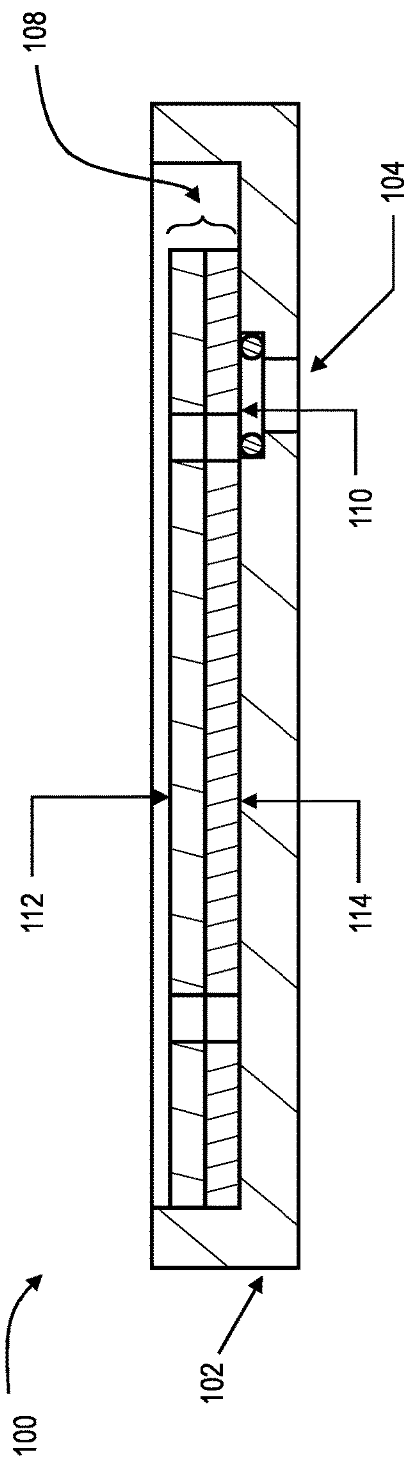
FIG. 1A is a cross-sectional side view of a non-magnetic thermal bimetal valve system according to an aspect of the present disclosure.
Figure 1B:
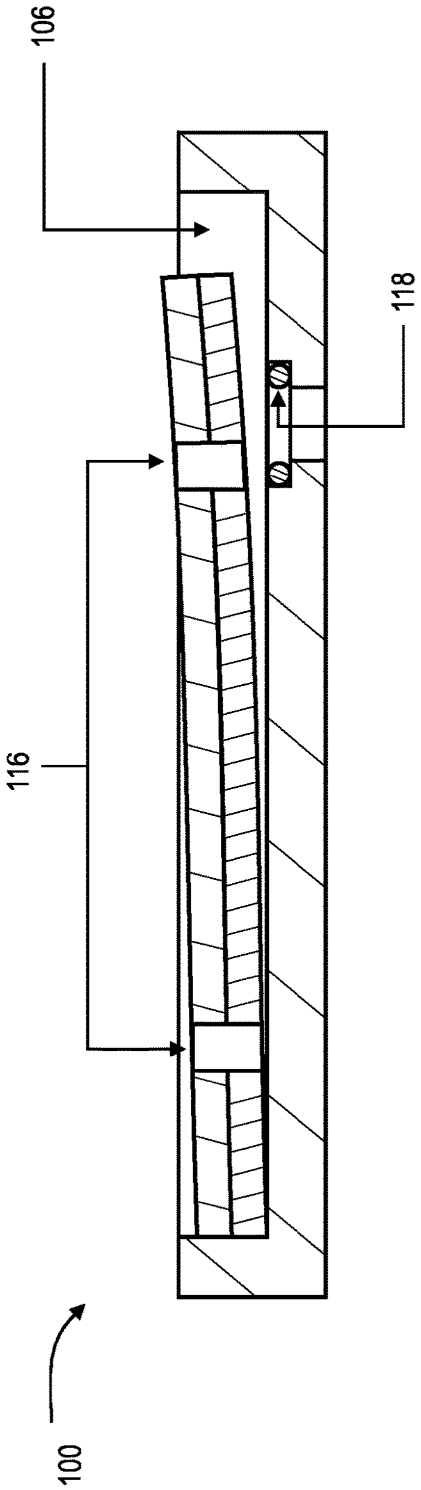
FIG. 1B is a cross-sectional side view of a non-magnetic thermal bimetal valve system according to an aspect of the present disclosure.

With reference to FIGS. 1A and 1B, the basic principles of operation of a non-magnetic bimetal valve 100 are illustrated. According to the present disclosure, the bimetal valve 100 can include a housing 102 that includes one or more fluid communication openings 104 (e.g., inlets and/or outlets) and defines an interior volume or portion 106 of the valve 100. The fluid communication openings 104 allow for the flow of a fluid (such as a gas or aqueous solution), to pass through the valve 100. In certain aspects, the pressure and flow rate of the fluid flow can depend on the composition and/or purpose of the fluid flow. For example, and without limitation, the fluid flow can comprise room air and have a flow rate of about 1 L/minute at about 300 mmHg or the fluid flow can comprise $CO_2$, $O_2$, and/or an anesthetic agent(s) and have a flow rate of about 200 mL/minute at about 100 mmHg.

The bimetal valve 100 further includes a bimetal actuator 108 that is disposed within the open interior volume 104 of the valve 100 and forms a fluid-tight seal 110 with at least one of fluid communication openings 104. The bimetal actuator 108 can be mechanically secured to the housing 102, for example and without limitation, by heat staking, screws, overmolding, and the like. In some embodiments, the bimetal valve 100 can also include one or more gaskets 118 disposed within a seat associated with one or more fluid communication openings 104 of the housing 102, which assists in the formation of the fluid-tight seal 110.

According to the present disclosure, the bimetal actuator 108 can include a first or active member 112 and a second or passive member 114. Each of the active and passive members 112, 114 can comprise a metal and/or metal alloy. In particular embodiments, the metal and/or metal alloys of the active and passive members 112, 114 are non-magnetic and are different such that the active member 112 has a coefficient of thermal expansion that is different from the coefficient of thermal expansion of the passive member 114. In particular embodiments, the active member 112 can comprise a first non-magnetic metal and/or metal alloy. For example, and without limitation, the first non-magnetic metal and/or metal alloy can include at least one of magnesium, manganese, nickel, titanium, copper, and the like. In specific aspects, the first non-magnetic metal and/or metal alloy can comprise nitinol (NiTi). Similarly, the passive member 114 can comprise a second non-magnetic metal and/or metal alloy. For example, and without limitation, the second non-magnetic metal and/or metal alloy can include at least one of magnesium, manganese, nickel, titanium, copper, and the like. In specific aspects, the second non-magnetic metal and/or metal alloy can comprise nitinol (NiTi). In other aspects, the active member 112 and/or passive member 114 can be substantially free from at least one of iron, nickel, steel, cobalt, or other magnetic metals. As used herein, the active member 112 and passive member 114 are substantially free from magnetic metal(s) when it has less than 0.1 wt % of said magnetic metal(s).

As shown in FIGS. 1A and 1B, the active member 112 and the passive member 114 can be physically joined to one another. In particular, the active member 112 and the passive member 114 can be joined together using one or more constraint devices 116. For example, and without limitation, the constraint device 116 can be a mechanical constraint device or method, such as a welding joint, brazing joint, and a rivet. In other words, the active member 112 and the passive member 114 can be welded together, brazed together, and/or rivetted together.

As mentioned above, the bimetal actuator 108 can be configured to form a fluid-tight seal 110 with at least one of the fluid communication openings 104 of the valve 100, as shown in FIG. 1A. However, as shown in FIG. 1B, the bimetal actuator 108 can be operated to release the fluid-tight seal 110 with the at least one fluid communication opening 104 and permit the flow of a fluid, such as a gas or aqueous solution, into and through the open volume 106 of the valve 100. In alternative embodiments, the bimetal actuator 108 can be operated to create a fluid-tight seal 110 with at least one of the fluid communication openings 104 upon activation, rather than be configured to release the fluid-tight seal 110 upon activation.

As used herein, operating and/or actuating the bimetal actuator 108 refers to changing the temperature of at least the active member 112 of the bimetal actuator 108. In particular embodiments, this can be achieved through one or more methods, such as direct heating and/or by passing an electrical current through at least the active member 112. Because the active member 112 has a different coefficient of thermal expansion than the passive member 114, the active and passive members 112, 114 deform in different amounts, which thereby engages or releases the fluid-tight seal 110. In some embodiments, the active member 112 has a first coefficient of thermal expansion that is greater than the second coefficient of thermal expansion of the passive member 114. In certain embodiments, the bimetal actuator has a ratio of the first coefficient of thermal expansion to the second coefficient of thermal expansion that is from about 11:10 to about 100:1. In further embodiments, the ratio of the first coefficient of thermal expansion to the second coefficient of thermal expansion is at least about 15:10, at least about 2:1, at least about 5:1, at least about 10:1, at least about 25:1, at least about 50:1, or at least about 75:1.

Figure 2:
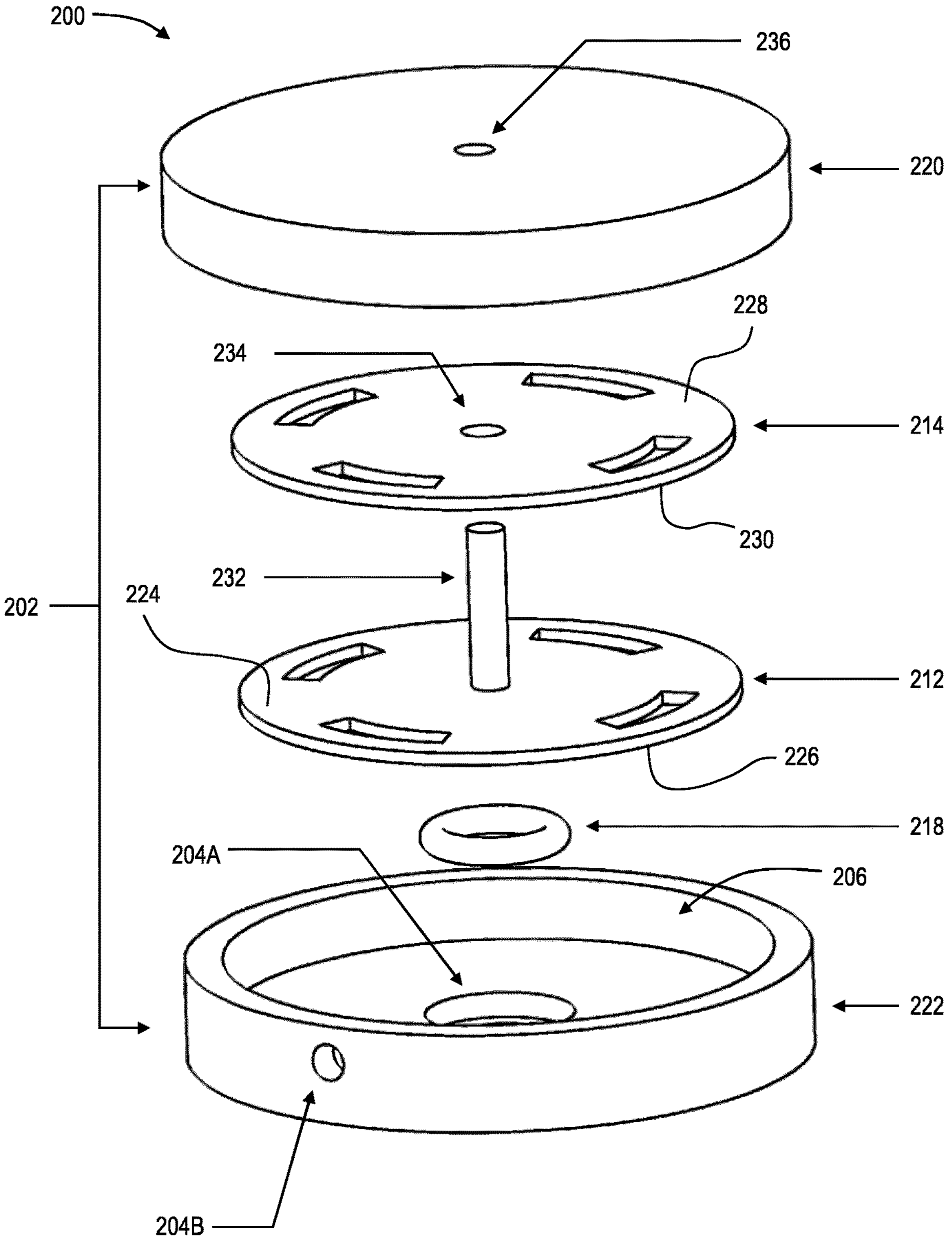
FIG. 2 is an exploded view of a first non-magnetic thermal bimetal valve system having circular disc actuators according to an aspect of the present disclosure.
Figure 3:
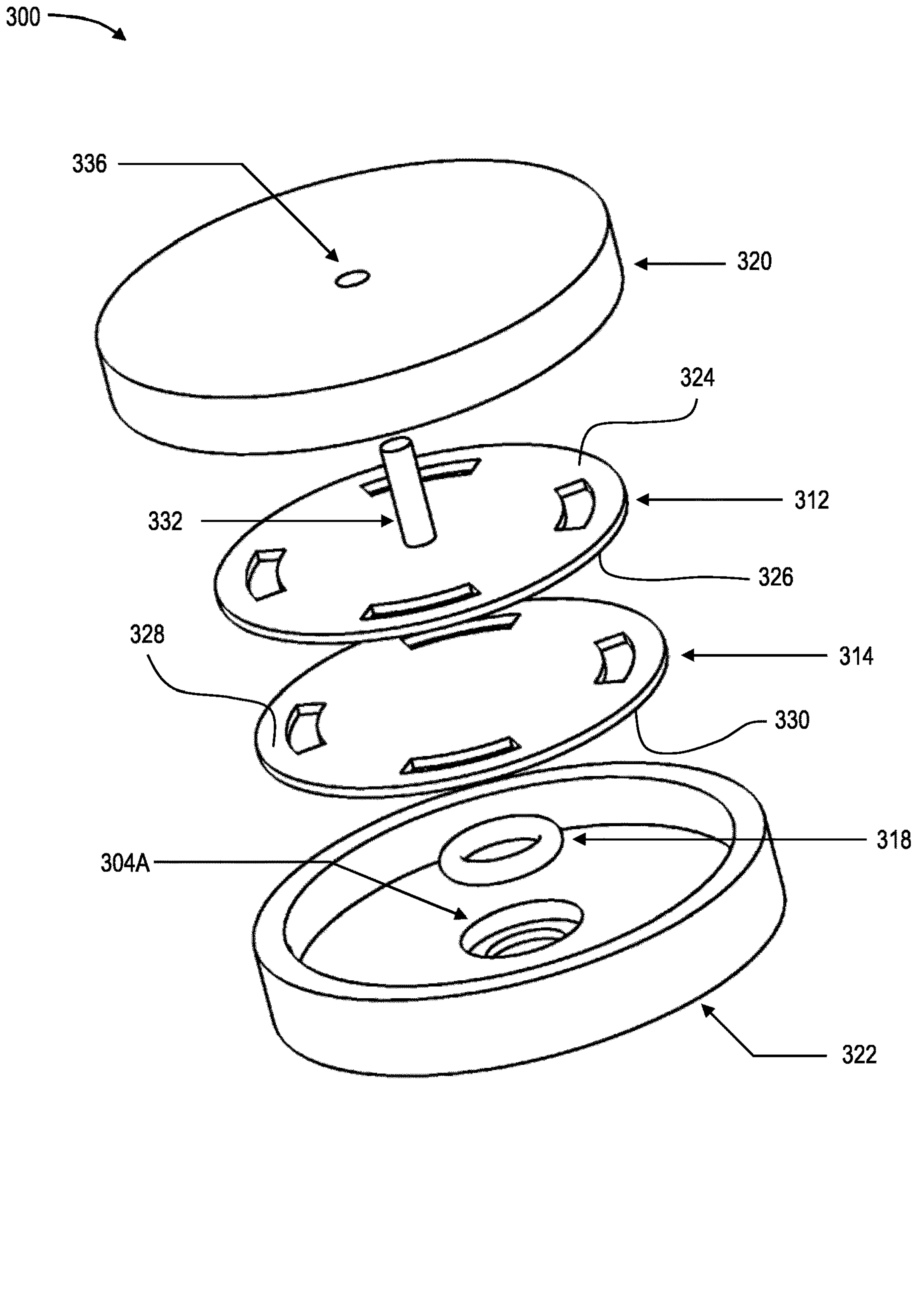
FIG. 3 is an exploded view of a second non-magnetic thermal bimetal valve system having circular disc actuators according to an aspect of the present disclosure.
Figure 4:
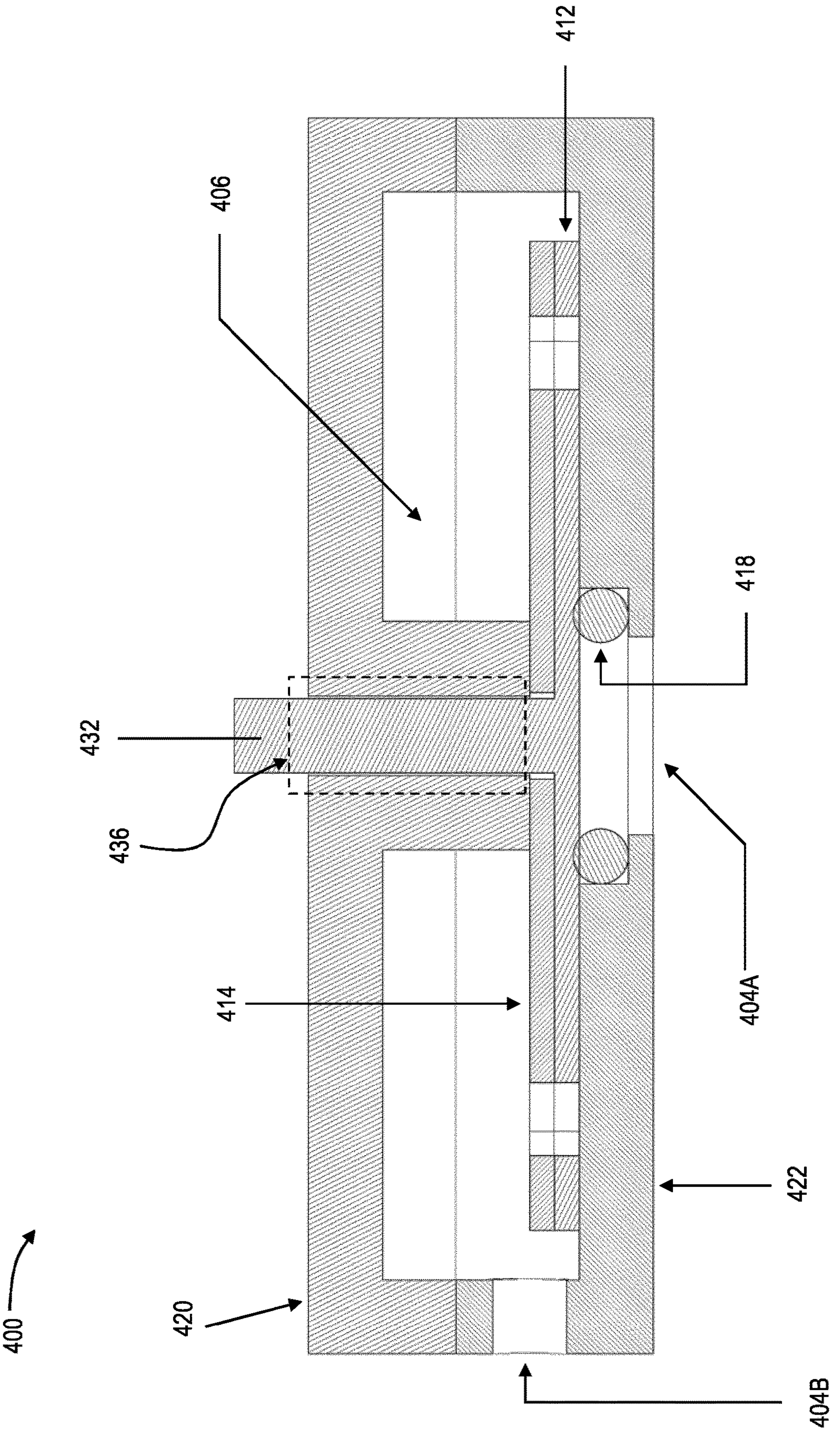
FIG. 4 is a cross-sectional side view of the first non-magnetic thermal bimetal valve system shown in FIG. 2.

Turning to FIGS. 2-4, two embodiments of a non-magnetic thermally-controlled valve are illustrated according to various aspects of the present disclosure.

With reference to FIG. 2, an exploded perspective view of a non-magnetic thermally-controlled valve 200 is illustrated. The non-magnetic thermally-controlled valve 200 includes a valve housing 202 that is formed from a non-magnetic material such as a plastic. The valve housing 202 can include at least a first fluid communication opening or outlet 204A and a second fluid communication opening or inlet 204B. Further, as shown, the valve housing 202 can comprise two or more components, such as a first portion 220 and a second portion 222, that join together to define an interior open volume or portion 206 within the housing 202. Although the fluid communication openings 204A, 204B are shown as part of the second portion 222 of the valve housing 202, other embodiments of the housing 202 are contemplated, such a first portion 220 of the housing 202 comprising one or more of the fluid communication openings 204A, 204B. Additionally, the valve system 200 is not limited to just two fluid communication openings 204A, 204B, but can include three or more fluid communication openings, such as two or more outlets 204A and two or more inlets 204B.

The non-magnetic thermally-controlled valve 200 also includes a bimetal actuator comprising an active member 212 and a passive member 214. As shown in FIG. 2, the active and passive members 212, 214 of the bimetal actuator can be disc-shaped rather than cantilever beam-shaped, as shown in FIG. 1. The active member 212 can include a first surface 224 and an opposing second surface 226, the passive member 214 can include a first surface 228 and an opposing second surface 230, and the active member 212 and the passive member 214 can be constrained together at the first surface 224 of the active member 212 and the adjacent second surface 230 of the passive member 214. Further, the active member 212, or a portion thereof (such as the second surface 226), can engage a gasket 218 disposed within a portion of the opening 204A in order to form a fluid-tight seal. In particular embodiments, the bimetal actuator can similarly engage one or more additional fluid communication openings 204A, 204B and be actuated to engage or release additional fluid-tight seals of the valve housing 202.

As discussed above, the bimetal actuator of the non-magnetic thermally-controlled valve 200 can be actuated in order to engage or release one or more fluid-tight seals by heating at least the active member 212 of the bimetal actuator. As shown in FIG. 2, this can be accomplished using a heating lead 232 operatively connected to the active member 212. The heating lead 232 can comprise a material suitable for transferring heat to the active member 212. For example, and without limitation, the heating lead 232 can comprise the same material used to form the active member 212, or can comprise copper wire. In particular embodiments, the heating lead 232 of the active member 212 extends through a cutout 234 of the passive member 214 and a receiving aperture 236 of the valve housing 202, such as the receiving aperture 236 of the first portion 220 of the valve housing 202. Although the heating lead 232 is shown placed in the middle of the active member 212, the heating lead 232 can also be placed in alternative locations. Regardless, as shown in FIG. 4, the heating lead 232 can form a fluid-tight seal with the receiving aperture 236 of the valve housing 202.

In particular embodiments, the heating lead 232 can be operatively connected to an external valve controller (not shown) that is configured to actuate the bimetal actuator and/or a heat generating source (not shown) that is configured to electrically and/or thermally regulate the temperature of at least the active member 212. In some embodiments, the heat generating source can be further connected to the valve controller and/or the external valve controller can comprise the heat generating source. The external valve controller can actuate the bimetal actuator by heating the active member 212 of the bimetal actuator using the heating lead 232, either by directly heating the heating lead 232 and/or by passing an electrical current through the heating lead 232, for example. As described here, the valve controller can be formed of one or multiple modules and can be configured to operate the valve 200 in response to an input, such as input obtained via user input device or an input from one or more sensors within the device. The controller can comprise, for example, a processor and a memory, and can optionally include a connectivity module. The processor can take any suitable form, including but not limited to a microcontroller, multiple microcontrollers, circuitry, a single processor, or plural processors. The memory can take any suitable form, including a non-volatile memory and/or RAM. The non-volatile memory can include read only memory (ROM), a hard disk drive (HDD), or a solid-state drive (SSD). The memory can store, among other things, an operating system as well as sensor data from sensor(s). The RAM is used by the processor for the temporary storage of data. According to some embodiments, an operating system can contain code which, when executed by the valve controller, controls operation of the hardware components of the valve system 200.

With reference to FIG. 3, another non-magnetic thermally-controlled valve 300 is illustrated according to the present disclosure. Here, the valve 300 includes a bimetal actuator comprising an active member 312 and a passive member 314. However, the active member 312 and the passive member 314 of the bimetal actuator can be arranged such that the passive member 214 or a portion thereof engages a gasket 318 disposed within a portion of a fluid communication opening 304A in order to form a fluid-tight seal with the valve housing 302 (or a portion thereof such as housing portion 322). As such, the active member 312 can have a first surface 324 and a second surface 326, the passive member 314 can have a first surface 328 and a second surface 330, and the active member 312 and the passive member 314 can be joined at the second surface 326 of the active member 312 and the first surface 328 of the passive member 314. In some of these embodiments, the heating lead 332 of the active member 312 does not pass through the passive member 314 but can still engage a receiving aperture 336 of the valve housing 302 (or a portion thereof such as the first portion 320).

Regardless of whether the active member 212, 312 or the passive member 214, 314 forms a fluid-tight seal with one or more of the fluid communication openings 204A, 304A, the active member 212, 312 and the passive member individual comprise a non-magnetic metal and/or metal alloy such that the active member 212, 312 has a coefficient of thermal expansion that is greater than the coefficient of thermal expansion of the passive member 214, 314. As such, the passive member 214, 314 acts to pull the active member 212, 312 back into an original position (either engaging or releasing a fluid-tight seal) once the active member 212, 312 is no longer active.

Turning now to FIG. 4, shown is a non-magnetic thermally-controlled valve 400 with an active member 412 forming a fluid-tight seal with a gasket 418 over a fluid communication opening 404A. According to various aspects of the present disclosure, valve 400 includes: a valve housing comprising a first housing portion 420 and a second housing portion 422; a first fluid communication opening 404A; a second fluid communication opening 404B; and an interior open volume/portion 406 defined by the housing portions 420, 422. The passive member 414 of the bimetal actuator is joined with the active member 412 and sits on top of the active member 412 such that the heating lead 432 of the active member 412 extends through a receiving aperture 436 of formed by the first portion 420 of the valve housing.

Figure 5:
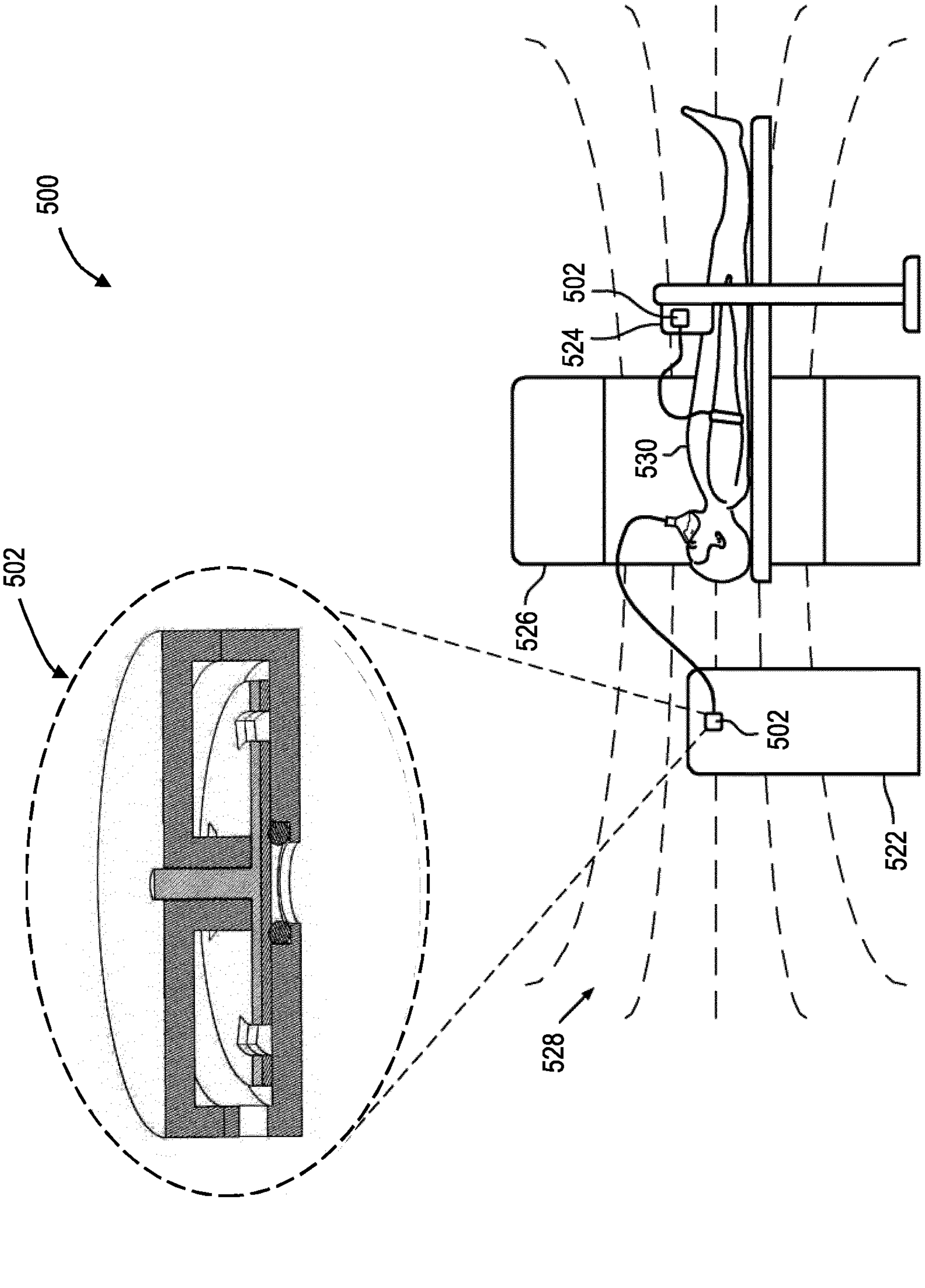
FIG. 5 is a schematic illustrating an embodiment of a non-magnetic thermal bimetal valve in a strong magnetic field according to aspects of the present disclosure.

Also described herein are magnetic resonance ("MR") systems incorporating a non-magnetic thermally-controlled valve for use an environments with a strong magnetic field, such as magnetic resonance system 500 illustrated in FIG. 5. A magnetic resonance device, such as the MR scanner 526, can generate strong magnetic fields 528 such as a static main magnetic field, gradient magnetic fields, radio frequency ("RF") pulses, and the like. In particular embodiments, the non-magnetic thermally-controlled valve 502 can be used to regulate the delivery of fluids such as anesthetic gases to a subject 530, monitoring gases expired by the subject 530, monitoring the blood pressure of the subject 530, and the like. As shown, two medical devices with a non-magnetic thermally-controlled valve 501 that can provide a fluid flow are shown, by way of example and without limitation, including an anesthesia device 522 and a non-invasive blood pressure (NIBP) measuring device 524.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

It should also be understood that, unless clearly indicated to the contrary, in any methods claimed herein that include more than one step or act, the order of the steps or acts of the method is not necessarily limited to the order in which the steps or acts of the method are recited.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A non-magnetic thermally-controllable valve, comprising:

a valve housing, comprising an outlet, an inlet, and an open interior volume; and a bimetal actuator disposed within the open interior volume of the valve housing and forming a fluid-tight seal with at least one of the inlet and the outlet, wherein the bimetal actuator comprises an active member and a passive member, the active member being physically joined to the passive member;

wherein the active member comprises a first non-magnetic metal and has a first coefficient of thermal expansion, the passive member comprises a second non-magnetic metal and has a second coefficient of thermal expansion, and the first coefficient of thermal expansion is greater than the second coefficient of thermal expansion.

2. A magnetic resonance system, comprising:

a magnetic resonance device;

a fluid flow device comprising a non-magnetic thermally-controlled valve, wherein the non-magnetic thermally-controlled valve includes:

a valve housing comprising an inlet, an outlet, and an open interior volume; and a bimetal actuator disposed within the open interior volume of the valve housing and forming a fluid-tight seal with at least one of the inlet and the outlet, wherein the bimetal actuator includes an active member and a passive member, the active member being physically joined to the passive member; and a valve controller operatively connected to the non-magnetic thermally-controlled valve, the valve controller being configured to actuate the bimetal actuator of the non-magnetic thermally-controlled valve.

3. The non-magnetic thermally-controlled valve of claim 1, wherein the first non-magnetic metal comprises at least one of: magnesium; manganese; nickel; titanium; or copper.

4. The non-magnetic thermally-controlled valve of claim 1, wherein the second non-magnetic metal comprises at least one of: magnesium; manganese; nickel; titanium; or copper.

5. The non-magnetic thermally-controlled valve of claim 1, wherein the first non-magnetic metal is substantially free from at least one of: iron; nickel; cobalt; or steel.

6. The non-magnetic thermally-controlled valve of claim 1, wherein the second non-magnetic metal is substantially free from at least one of: iron; nickel; cobalt; or steel.

7. The non-magnetic thermally-controlled valve of claim 1, wherein the bimetal actuator has a ratio of the first coefficient of thermal expansion to the second coefficient of thermal expansion that is from about 11:10 to about 100:1.

8. The non-magnetic thermally-controlled valve of claim 1, wherein the active member is at least one of: a cantilever beam; a disc; or a plunger.

9. The non-magnetic thermally-controlled valve of claim 1, wherein the passive member is at least one of: a cantilever beam; a disc; or a plunger.

10. The magnetic resonance system of claim 2, wherein the active member comprises a first non-magnetic metal and has a first coefficient of thermal expansion, the passive member comprises a second non-magnetic metal and has a second coefficient of thermal expansion, and the first coefficient of thermal expansion is greater than the second coefficient of thermal expansion.

11. The magnetic resonance system of claim 10, wherein the bimetal actuator has a ratio of the first coefficient of thermal expansion to the second coefficient of thermal expansion that is from about 11:10 to about 100:1.

* * * * *